United States Patent [19]

Menges et al.

[11] Patent Number: 4,491,133

[45] Date of Patent: Jan. 1, 1985

[54] FOLDING CARTRIDGE FOR A MULTIPLE CLIP APPLIER

[75] Inventors: John R. Menges, Woodbridge; Laszlo Huebscher, New Brunswick, both of N.J.

[73] Assignee: Ethicon, Inc., Somerville, N.J.

[21] Appl. No.: 345,975

[22] Filed: Feb. 5, 1982

[51] Int. Cl.³ .................. A61B 17/12; B25C 5/02
[52] U.S. Cl. ..................... 128/326; 128/325; 227/120
[58] Field of Search .......... 227/DIG. 1 A–DIG. 1 C, 227/120; 128/325–326; 604/61–64; 29/243.5, 243.56; 206/339–340

[56] References Cited

U.S. PATENT DOCUMENTS

| | | | |
|---|---|---|---|
| 3,665,924 | 5/1972 | Noiles et al. ........................ | 128/305 |
| 3,907,193 | 9/1975 | Heller ................................... | 220/339 |
| 4,296,751 | 10/1981 | Blake et al. ......................... | 128/325 |
| 4,316,468 | 2/1982 | Klieman ............................... | 128/325 |
| 4,430,997 | 2/1984 | Di Giovanni et al. ............... | 128/326 |

Primary Examiner—C. Fred Rosenbaum
Assistant Examiner—Gene B. Kartchner
Attorney, Agent, or Firm—Donal B. Tobin

[57] ABSTRACT

A folding cartridge for a plurality of ligating clips adapted for removable attachment to a multiple ligating clip applier. The folding portion of the cartridge may be easily fabricated flat as a unit and then the sidewalls may be folded to form a generally U-shaped channel. Special transfer fingers are suspended at the front of the folding rack by a combined leaf spring and torsion spring support for assisting in the proper control of ligating clips as they proceed from the cartridge to the applier.

14 Claims, 10 Drawing Figures

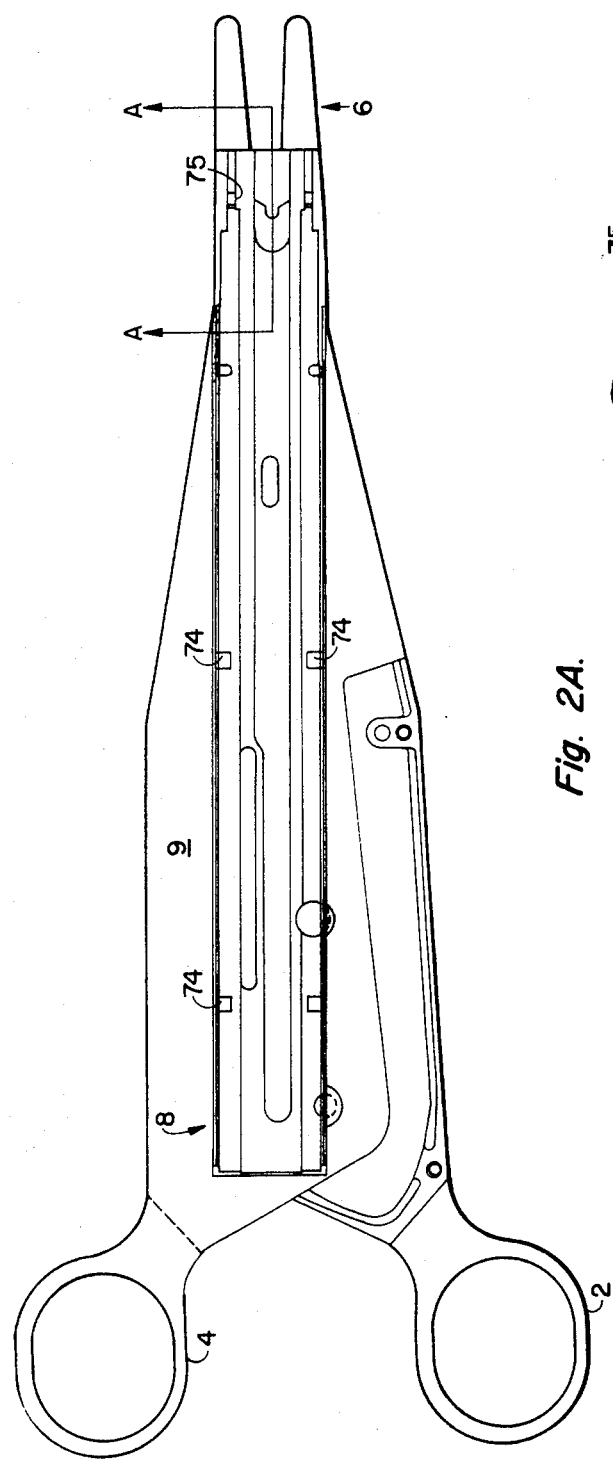
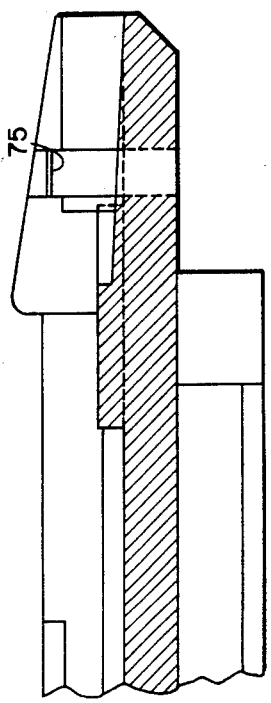
Fig. 2.
Fig. 2A.

4,491,133

FOLDING CARTRIDGE FOR A MULTIPLE CLIP APPLIER

BACKGROUND OF THE INVENTION

The present invention relates to an apparatus for applying surgical clips and, more particularly, to a folding cartridge for clips used with a multiple clip applier.

A separate Application Ser. No. 345,976 now U.S. Pat. No. 4,478,220, filed the same day as this application and assigned to the assignee as this application, is directed to a different cartridge used with a multiple clip applier. Since the disclosure of that application relates to a multiple clip applier which is used with a different cartridge but which, with certain minor modifications, can also be used with the cartridge of the present invention, the disclosure of that application is incorporated herein by reference in its entirety. As pointed out in the referenced application, it is desirable to have a multiple clip applier that can be operated with one hand using a familiar scissor-type action of a hemostat to provide good motor control for the surgeon while the clip is placed about a vessel and while the clip is closed to seal off the vessel. It is desirable to have a larger magazine of clips so that the surgeon does not have to change cartridges often during an operation. It is also desirable to have a cartridge which can be manufactured efficiently, at a low cost and in large scale production so that the cartridge may be made in a completely disposable form so that after the cartridge has been used, it may merely be thrown away.

SUMMARY OF THE INVENTION

The present invention provides a cartridge which can house a larger number of clips and which may be removably affixed to a scissors-type handle. The scissors-type handle is similar to the scissors-type handle of the referenced patent application except that the U-shaped channel on the back of the handle portion of the multiple clip applier is slightly modified to accept the clip in a slightly different fashion, which will be explained later in connection with the description of the preferred embodiment.

The cartridge itself includes a fixed rack housing and a moving rack housing which interlocks with the fixed rack housing and which can reciprocate longitudinally on the fixed rack housing in response to the drive mechanism on the multiple clip applier itself.

The fixed rack housing includes a base section, right and left sidewalls and a hinge connecting the sidewalls to the base so that the walls and the base can be fabricated flat as a unit and then the walls may be folded to form a generally U-shaped channel. A U-shaped moving rack housing interlocks with the fixed rack housing sidewalls. The sidewall hinge includes a V-shaped axial notch extending along the joint between the sidewall and the fixed rack housing base on the outside of the fixed rack housing. A recess on the base of the fixed rack housing on the inside of the hinge extends axially along the cartridge with the lateral outside corner of the rectangular recess aligned generally with the bottom of the V-shaped notch to define a hinge point for the sidewall. A protuberance with a mating configuration to the recess is formed on the inside of the sidewall bordering the recess so that when the hinge is closed and the sidewall is rotated perpendicular to the fixed rack housing to form a U-shaped channel, the adjacent sides of the protuberance and the recess move together to form a support for holding the wall perpendicular to the fixed rack housing base. An axial flange on the inside of each fixed rack housing sidewall forms a track in which an outwardly projecting flange for the moving rack housing fits in interlocking relationship.

The base of the fixed rack housing and moving rack housing each support pairs of fingers extending toward one another in confronting relationship for holding the clips in position between the two racks. Transfer fingers are disposed at the front end of the fixed rack housing for transferring clips through the cartridge and are supported by a combined leaf spring and torsion spring which control the motion of the transfer fingers with respect to the plane of the fixed rack housing and which incorporates a tie-bar to restrict the independent movement of the transfer fingers. The transfer finger support system may extend from a single rod extending forward from the front end of the fixed rack housing base. The transfer fingers include a generally wedge-shaped configuration with the apex of the wedge aligned generally with the base of the fixed rack housing and rising to a plane spaced vertically above the plane of the fixed rack housing base. The second plane extends axially for a short distance to the front end of each transfer finger. The second plane of the transfer finger includes a protrusion for engaging a portion of the clip for holding the clip in position even though the applier mechanism may be moved slightly when the user is in the process of fixing a clip about a vessel.

The fingers which project from the bases of the fixed and moving racks can be formed in two embodiments. In the first embodiment, the fingers are formed integrally with the respective rack bases and are positioned in apertures in the base and hinged from one edge of the aperture. The hinge may include a wedge-shaped brace to strengthen the hinge. The fingers may also include an extension which spaces the finger somewhat away from the edge of the aperture and cantilevers the finger from the edge of the aperture. In a further alternative embodiment, the fingers may be stamped into separate metal strips, which strips have a number of flanges extending from their longitudinal sides. In this embodiment, the sides of the fixed rack and moving rack housings are equipped with corresponding openings to receive the flanges extending from the edges of the metal strips to lock the metal strips into the base of the fixed rack or moving rack housings, respectively.

The fixed rack housing may also include special detents for holding the front end of the fixed rack housing into intimate engagement with the U-shaped channel of the multiple clip applier to provide added stability to the clip support system as the clip is transferred from the cartridge to the multiple clip applier.

BRIEF DESCRIPTION OF THE DRAWINGS

These and other advantages and features of the present invention will become apparent from the following description of certain embodiments taken in conjunction with the following drawings in which:

FIG. 2 shows a plan view of the back of the multiple clip applier to which the cartridge of the present invention may be attached;

FIG. 2A shows a section taken along lines A—A in FIG. 2;

DETAILED DESCRIPTION OF THE PREFERRED EMBODIMENT

Figure 1:
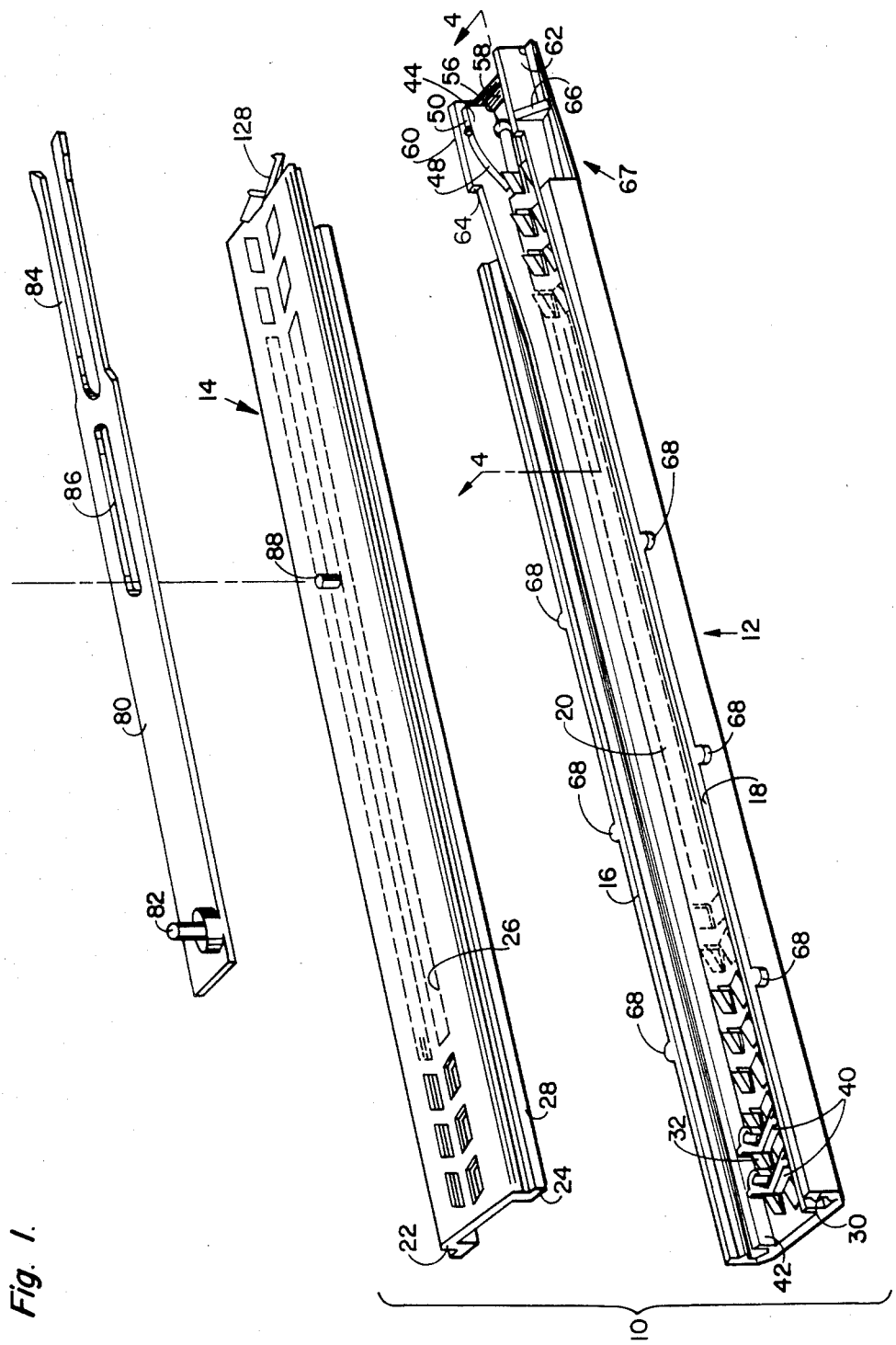
FIG. 1 shows an exploded perspective view of the cartridge of the present invention.

Referring now to FIG. 1, there is shown an exploded perspective view of the cartridge 10 of the present invention which includes a fixed rack housing 12 and moving rack housing 14 which interlocks with fixed rack housing 12 so that it may reciprocate longitudinally along fixed rack housing 12. Fixed rack housing 12 has a left and right sidewall 16 and 18, respectively, and a base 20 defining a generally U-shaped channel configuration. Moving rack 14 has a left and right sidwall 22 and 24, respectively, and a base 26. As seen best in FIG. 3, sidewalls 22 and 24 of moving rack 14 each have an outwardly extending flange 28 which extends axially along the entire length of moving rack 14. The inside of each sidewall 16 and 18 of fixed rack 12 also includes an axially extending flange 30 disposed in confronting mating relationship with flange 28 to provide an interlocking relationship therebetween so that moving rack 14 may be supported for longitudinal reciprocal motion along fixed rack housing 12.

The bases 20 and 26 of the rack housings are equipped with a plurality of pairs of fingers 32 which project into the respective U-shaped spaces defined by the rack housings. These fingers 32 are flexible and extend along both of the rack housings. These fingers 32 may be molded into the base 20 or 26 of the rack housings or may be stamped into a separate piece of metal which may be bonded or otherwise affixed within fixed rack housing 12 or moving rack housing 14 as will be explained later in connection with FIG. 7. The shape and spacing of the fingers 32 will be discussed in greater detail in connection with FIGS. 4 and 6.

Referring again to FIG. 1, a plurality of ligating clips 40 are placed between adjacent pairs of fingers 32. The fingers on the moving rack slightly interfere with the fingers on the fixed rack so that as moving rack 14 reciprocates with respect to fixed rack 12, clips 40 are indexed forward one space. Guides 42 extend axially along base 20 of fixed rack housing 12 to provide transverse support for aligning clips 40 within fixed rack 12.

Transfer fingers 44 are supported on the forward end of base 20 of fixed rack housing 12 by means of combined, generally T-shaped leaf spring/torsion spring 46. (See FIG. 5.) Transfer fingers 44 are generally wedge-shaped in configuration with the apex of the wedge aligned with the base 20 of fixed rack housing 12. (See FIG. 4.) The incline 48 of wedge 44 rises from the plane of base 20 to a second plane 50 aligned generally parallel to plane 20 but spaced apart from it. Pawl 51 is mounted on second plane 50 of each transfer finger 44 to hold a clip 40 in position while a surgeon may manipulate the multiple clip applier in the process of placing a ligating clip 40 about a vessel.

Referring again to FIG. 5, each transfer finger 44 is separately supported by its own rod 47, which has an axial portion 54 extending from the front of base 20 and a transverse portion 56 connected to axial portion 54 turns connected to the inside surface 52 of transfer finger 44.

In the preferred embodiment shown in FIG. 1, the axially extending portion 54 of separate support rods 47 is combined into axial portion 54 which branches into two separate transverse portions 56.

Tie-bar 58 connects the front portions of the two transfer fingers 44 to restrict their independent motion with respect to one another. The axial portion 54 of spring 46 provides a leaf-spring type support bias for the transfer finger assembly, whereas, the transverse portion 56 or spring 46 provides a torsion-spring type bias support.

Referring again to FIG. 1, the transfer finger assembly extends from the front end of base 20 of fixed rack housing 12 and is enclosed by sidewall extensions 60 and 62 which extend axially from sidewalls 16 and 18, respectively. Each sidewall extension 60 and 62 incorporates a step 64 against which the front end of moving rack housing 14 may stop.

Hold-down tabs 66 extend outwardly from sidewall extension 60 and 62 and taper from the bottom of sidewalls 60 and 62 outwardly to the top surface 67 thereof. As will be explained further in connection with FIGS. 2 and 2A, hold-down tabs 66 fit into a corresponding slot on the multiple clip applier body to solidly support the front-end portion of cartridge 10 in the applier handle 9.

Also shown in FIG. 1 are a number of spaced-apart, outwardly-projecting tabs 68 located near the bottom edge of sidewalls 16 and 18 of fixed rack housing 12.

Figure 3:
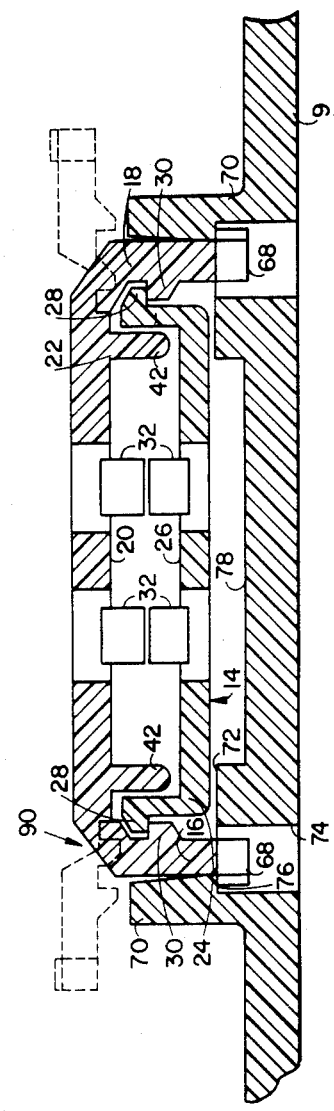
FIG. 3 shows an assembly drawing showing the cartridge of the present invention assembled to the handle of FIG. 2.

The assembled cartridge 10 is connected to a multiple clip applier as shown in FIGS. 2 and 3.

The multiple clip applier itself and the drive mechanisms associated with it for indexing clips through the cartridge and then for advancing clips out of the cartridge into the nose of the multiple clip applier is thoroughly explained in the referenced patent application (ETH-513). Only a limited summary of the handle portion of the multiple clip applier will be included in this application.

As shown in FIG. 2, the multiple clip applier is shaped like a scissors, with ringe handles 2 and 4 on one end, and a nose section 6 on the other. A U-shaped channel 8 is integrally disposed on the rear surface of the multiple clip applier body 9.

As shown in FIG. 3, the sidewalls 70 of U-shaped channel 8 extend integrally from the body 9 of the multiple clip applier.

The base 72 of U-shaped channel 8 includes a number of openings 74 located at the inside edge of walls 70. Holes 74 may pass all the way through body 9 or may be mere recesses in body 9. The outside edge of holes 74 undercut the inside edge of wall 70 so as to provide an undercut lip 76.

Tabs 68 on the outside surface of the sidewalls 16 and 18 of fixed rack housing 12 are adapted to slide into holes 74 and engage undercuts 76 of sidewall 70 so as to hold fixed rack housing 12 in position in U-shaped channel 8. Undercut 76 and holes 74 are best shown in FIG. 3.

The hold-down tabs 66 on the sidewall extensions 60 and 62 of fixed rack housing 12 fit into corresponding undercuts 75 in the forward portion of U-shaped channel 8 shown best in FIG. 2A.

Central portion 78 of base 72 of U-shaped channel 8 forms a depression running axially along base 72 and provides a track along which pusher 80 may reciprocate longitudinally along body 9 adjacent cartridge 10 under the influence of the drive mechanism which is housed on main handle body 9 (see FIGS. 1 and 3). As explained in the referenced U.S. Pat. No. 4,478,220 pusher pin 82 projects through an opening (not shown) in body 9 into engagement with a drive mechanism supported on the other side of body 9 of the multiple clip applier. As shown in FIG. 1, the forward portion of pusher 80 includes fingers 84 which engage the back of a ligating clip 40 and take it from its position on transfer fingers 44 into the nose section 6 of the multiple clip applier. Pusher 80 includes a lost motion slot 86 which engages a lost motion pin 88 on the back of moving rack housing 14. Lost motion slot 86 and pin 88 permit a portion of the reciprocating motion of pusher 80 to be captured to drive moving rack housing 14 on a short-stroke reciprocating motion to index clips 40 through cartridge 10. An important feature of the present invention is the construction of fixed rack housing 12 which will now be discussed in connection with FIGS. 4, 5 and 6. Fixed rack housing 12 is preferably made of molded plastic and is fabricated flat and includes a base section 20 and left and right sidewalls 16 and 18. Left and right sidewalls 16 and 18 are joined to base 20 by means of a hinge 90 so that fixed rack housing 12 may be fabricated flat as a unit and then walls 16 and 18 may be folded to form a generally U-shaped channel. The unfolded fixed rack housing 12 is shown best in FIG. 6, which is a front-end view partly in section. Tabs 68 are shown at the outer extremeties of sidewalls 16 and 18. Hinge 90 is formed at the junction of sidewall 16 and base 20 of fixed rack housing 12. A similar hinge 90 is formed at the junction of sidewall 18 and base 20 of fixed rack housing 12. Hinge 90 includes a generally V-shaped notch 92 extending longitudinally along the entire top surface of fixed rack housing 12. Hinge 90 also includes a recess 94 formed on the opposite side of base 20 from notch 92. In the preferred embodiment, recess 94 has a generally rectangular cross-section and extends along the entire length of hinge 90. The lateral outside corner 96 of rectangular recess 94 is generally aligned with the base 98 of V-shaped notch 92. Hinge 90 provides a thin junction between base section 20 and sidewalls 16 and 18, respectively, so that side walls 16 or 18 may be rotated approximately 90° from their flat fabrication position to form a generally U-shaped channel.

Figure 6:
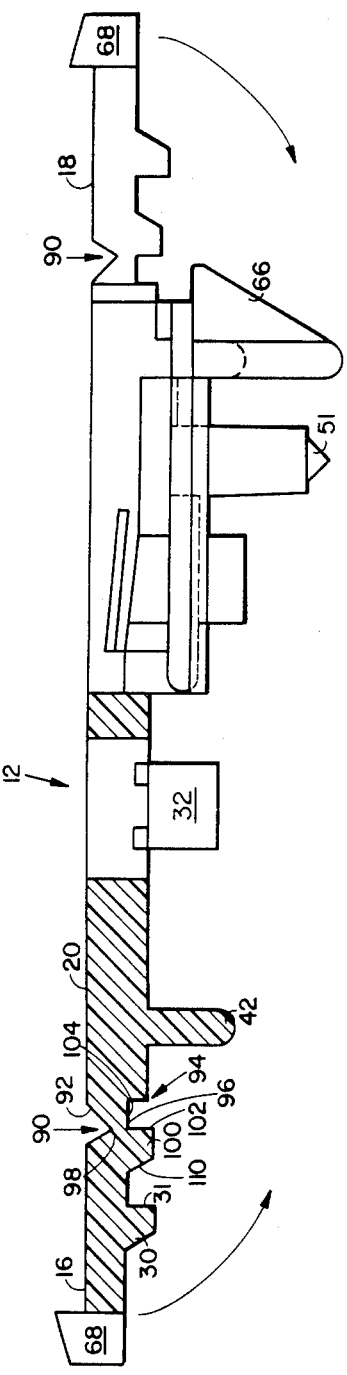
FIG. 6 shows a front view partly in cross-section of the cartridge of FIG. 5 taken along lines 6—6 in FIG. 5.

Still referring to FIG. 6, it can be seen that a protuberance 100 extends from the inside surface of sidewalls 16 and 18 adjacent rectangular recess 94. The shape of protuberance 100 and recess 94 are chosen so that when sidewalls 16 and 18 are folded at right angles to base 20, the side 102 of protuberance 100 rests against the bottom 104 of recess 94 to provide support for wall 16.

The inside surface of sidewalls 16 and 18 also includes a flange 30 against which flange 28 of moving rack housing 14 rests to form an interlocking track permitting moving rack 14 to reciprocate with respect to fixed rack 12. Side 31 of flange 30 closest to hinge 90 is aligned generally perpendicularly to inside surface of sidewalls 16 and 18 to provide a track against which similar flange 28 of moving rack housing 14 may rest. The adjacent side 110 of protuberance 100 is angled away from flange 30 to provide a larger clearance for flange 28 of moving rack housing 14. It can be seen, particularly in FIG. 3, that guide 42 forms a partial enclosure with the confronting surfaces of flange 30 to form a partially enclosed track for guiding moving rack housing 14 axially along fixed rack housing 12.

Figure 4:
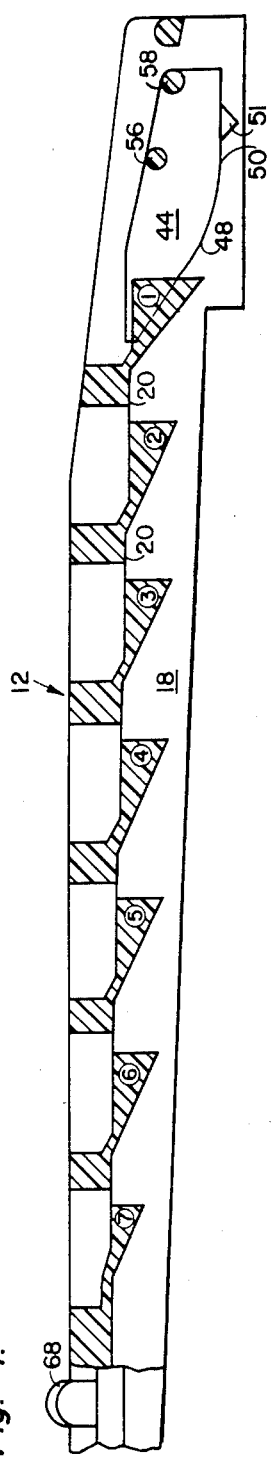
FIG. 4 shows a longitudinal cross-section of a portion of the cartridge of the present invention taken along lines 4—4 in FIG. 1.
Figure 5A:
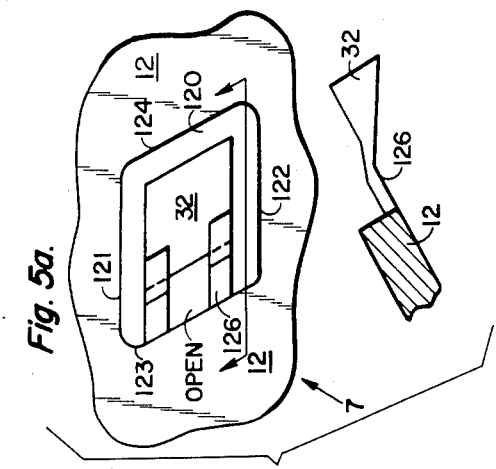
FIG. 5A shows a detail of FIG. 5.

The details of fingers 32 will now be discussed in connection with FIGS. 4 and 5. In FIG. 4, which is a partial cross-section of FIG. 1 taken along lines 4—4 in FIG. 1, it can be observed that the fingers 32 have a generally triangular cross-section whose forward face is aligned generally perpendicular to base 20 of fixed rack housing 12. As shown in the detail in FIG. 5A, each finger is suspended in an opening 120. The sides 121 and 122 of opening 120 are aligned generally parallel to the longitudinal axis of fixed rack housing 12, and sides 123 and 124 are aligned at an acute angle to the longitudinal center line of fixed rack housing 12 and parallel to each other. Each of fingers 32 is cantilevered from edge 123 of opening 120 by means of two braces 126.

Figure 5:
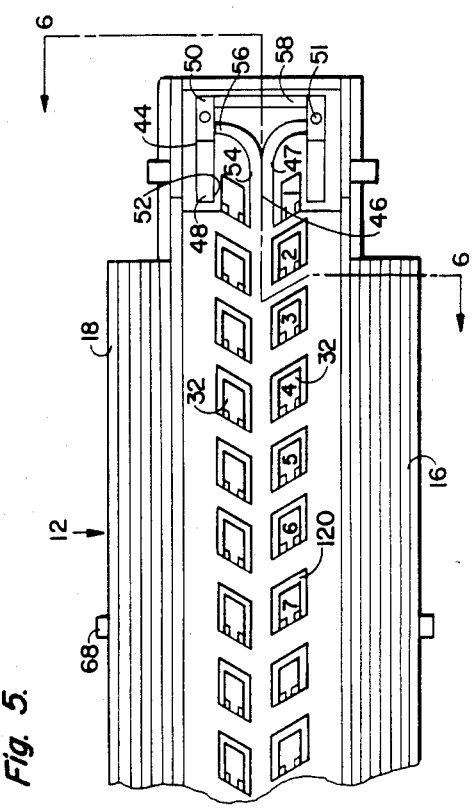
FIG. 5 shows a plan view of a portion of the cartridge of the present invention.

In FIGS. 4 and 5, each finger 34 is labeled with a number for purposes of clarity. It can be observed from FIG. 4 that the forward edge of triangular fingers 32 is aligned generally perpendicular to the base 20 of fixed rack housing 12. The forward-most finger has a larger vertical dimension than fingers 2 through 6 to facilitate the transfer of clips from one level to another within cartridge 10.

Fingers 2 through 6 all have a similar shape and height. The surface from which fingers 2 through 6 are suspended tapers at a small angle away from face 20 as one proceeds from the rear toward the forward end of fixed rack housing 12. The remaining fingers are all like finger 7 and are smaller than fingers 2 through 6 and are all aligned along base 20 and do not taper. Fingers 7 and those fingers behind it all preferably have the shape of the fingers shown in FIG. 5A.

The fingers of moving rack housing 14 are all the same as the fingers 7 of fixed rack housing 12, and the inside surface of the base 26 of rack 14 tapers at a small angle toward the taper of fixed rack 12 in the region near the forward end of moving rack 14. These two tapering surfaces taper toward one another so that as a clip advances forward, it is more clearly engaged by the cartridge 10. The forward fingers 128 of moving rack 14 are slightly different in configuration from the remainder of the moving rack fingers in that they do not have a generally triangular shape but are merely cantilevered configurations (see FIG. 1).

Figure 7:
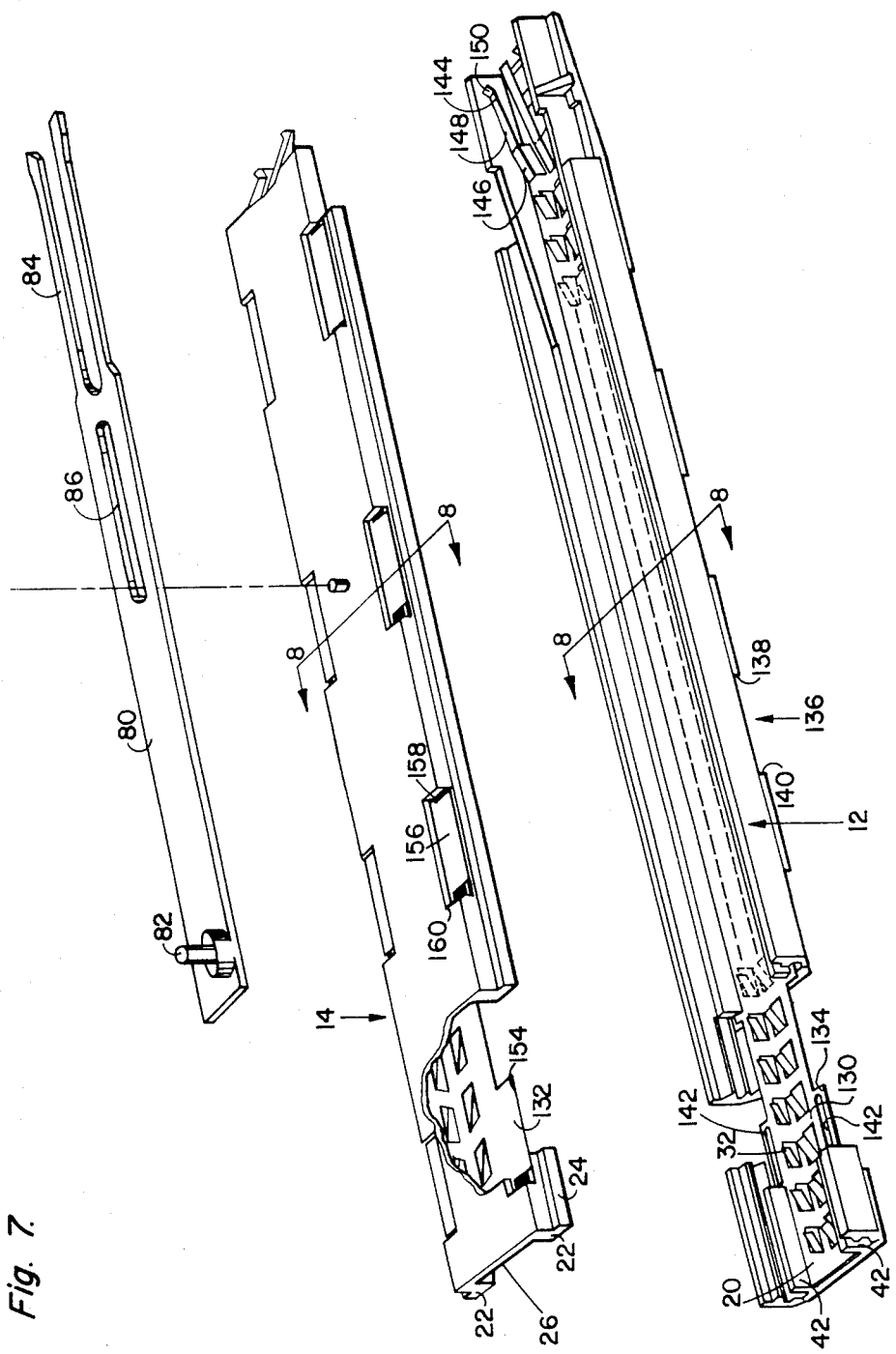
FIG. 7 shows an alternative embodiment of the cartridge shown in FIG. 1.
Figure 8:
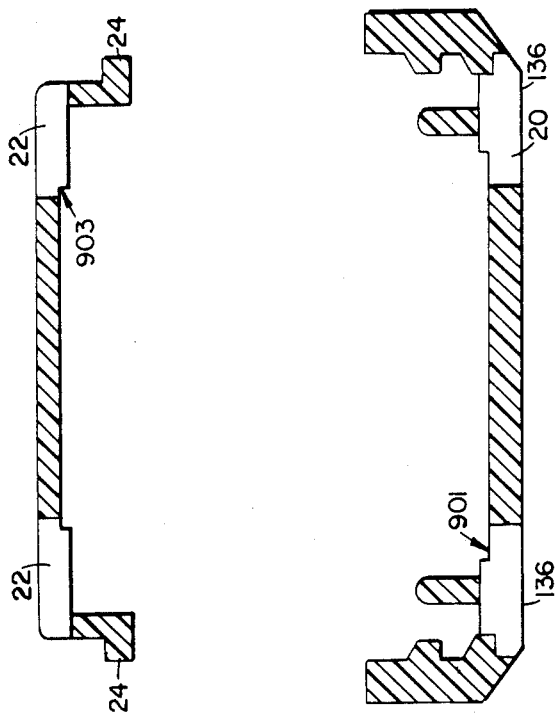
FIG. 8 shows a cross-section of the embodiment of FIG. 7 taken along lines 8—8 in FIG. 1.

Referring now to FIG. 7, there is shown an alternative embodiment of the finger configuration shown in FIG. 1. The fingers 32 of the embodiment shown in FIG. 1 are molded into the bases 20 and 26 of rack 12 and 14 respectively. Alternatively, the fingers may be stamped into metal strip 130 and 132, which may be affixed respectively into base 20 of fixed rack housing 12 and base 26 of moving rack housing 14, respectively. Metal strip 130 may be fixed into base 20 of fixed rack housing 12 by means of flanges 134 extending from the longitudinal side edges of strip 130. Base 20 has cutouts 136 which extend under guide rail 42. Side flange 134 extends into cutout 136 and under guide rail 42. The forward edge 138 and rear edge 140 of cutout 136 abut the corresponding edges of side flange 134 to prevent strip 130 from moving forward or backward. Side flanges 134 may have additional cutouts 142. Base 20 has a recess 901 for receiving strip 130 and preventing strip 130 from moving side to side (see FIG. 8.)

Transfer fingers 144 project from the forward end of strip 130 and extend in a first angled plane 146 and a second angled plane 148 to a third exit plane 150.

The metal strip 132 is positioned on base 26 of moving rack 14 by means of similar side flanges 154 which extend into similar cutouts 156 in the base 26 of moving rack 14. Strip 132 fits into similar recess 903 in base 26. Tight engagement between the forward edge 158 of cutout 156 and the rear edge 160 of cutout 156 with the respective confronting edges of side flange 154 prevent strip 132 from moving axially with respect to moving rack housing 14. Side flanges 154 extend out under the edges of sidewalls 22 of moving rack housing 14 to restrain metal strip 132 in that direction. The fingers extending from a metal strip 130 and 132 are similar in configuration to those fingers 32 on the embodiment of the fingers shown in FIG. 1. Each metal strip has a plurality of parallelogram-shaped openings therethrough with two of its sides at an acute angle to the longitudinal axis of the rack housing. Each finger is suspended from the rearward transverse sides of the opening. The fingers of both embodiments are cantilevered from the rear acute edge of the opening in which the fingers are disposed. The front edge of each finger is also tapered to be parallel to the acute surface from which the finger is cantilevered so that as the finger rises and falls, each part on the front edge of the finger moves the same vertical distance and stays in contact with the back of ligating clip 40 against which it is placed.

Otherwise the construction of the cartridge shown in FIG. 7 is the same as that shown in FIG. 1.

A clip 40 is indexed through the cartridge 10 in substantially the same fashion as clips are indexed through the cartridge of the referenced U.S. Pat. No. 4,478,220 using essentially the same drive mechanisms for the pusher 80 and the moving rack housing 14 to deliver clips to essentially the same nose section. A clip which is in the forward-most position on fixed rack housing 12 is indexed onto ramp 48 of transfer fingers 44. As the moving rack housing 14 comes forward the next time, transfer fingers 44 deflect against the bias spring action of axial leaf spring portion 54 and at the same time will tend to pivot about its own transverse axis against the bias force of torsion spring portion 56. Clip 40 will proceed onto second plane 50 in front of pawl 51. The next time pusher 80 comes forward, it will pick up the back of clip 40 and deliver it forward into the nose section 6 of handle body 9.

While the present invention has been described in connection with certain preferred embodiments, those skilled in the art will appreciate that certain modifications may be made without departing from the scope of the present invention. It is, therefore, not intended that the present invention be limited except as set forth in the following claims.

We claim:

1. A cartridge for a plurality of ligating clips, said cartridge comprising:
    a ligating clip applier having a body portion;
    a plurality of clips;
    a fixed rack housing adapted for removable attachment to and operable engagement with said multiple clip applier, and including a base section, right and left sidewalls and a hinge connecting said sidewalls to said base so that said walls and said base can be fabricated flat as a unit and then said walls may be folded to form a generally U-shaped channel along which said clips may be disposed;
    cooperating means on said body portion and said fixed rack housing for holding said fixed rack housing in said U-shaped channel configuration when attached to said body portion;
    a U-shaped moving rack housing disposed within said U-shaped channel of said fixed rack housing sidewalls and adapted for axial reciprocation along said fixed rack housing;
    cooperating guide means on said fixed rack housing and said moving rack housing for guiding said moving rack housing as it moves axially of said fixed rack housing;
    axial guides on said fixed rack housing base spaced apart from said sidewalls for aligning said ligating clips therebetween.

2. The cartridge of claim 1 wherein said sidewall hinge includes a generally V-shaped axial notch extending axially along the joint between the sidewall and the fixed rack housing base on the outside of said fixed rack housing;
    a recess on the base of said fixed rack housing on the inside of said hinge extending axially along said cartridge, the lateral outside corner of said rectangular recess aligned generally with the bottom of said V-shaped notch and defining the hinge point for said sidewall;
    a protuberance on the inside of said sidewall and bordering said recess so that when said hinge is closed to rotate said sidewall to form said fixed rack housing into a U-shaped channel, the adjacent sides of said protuberance and said recess moved together to form a support for holding said wall in generally perpendicular alignment with respect to said fixed rack housing base.

3. The cartridge of claim 1 wherein said interlock between said fixed rack housing and said moving rack housing includes an inwardly projecting, axially extending flange on the inside of each sidewall of said fixed rack housing, the surface of said flange disposed closest to the base of said fixed rack housing forming approximately a right angle with its sidewall;
    the surface of said hinge protuberance confronting said flange right angle wall being spaced apart therefrom to form a recess track for receiving said moving rack housing in interlocking relationship;
    the surface of said hinge protuberance tapering away from said flange right angle wall to provide greater clearance for said moving rack interlocking means; and,
    said moving rack housing including an outwardly extending flange on the outside surface of said moving rack sidewalls and slidably disposed in said interlocking track of said fixed rack housing sidewall.

4. The cartridge of claim 1 wherein said multiple clip applier body includes a handle portion;
    a generally U-shaped cartridge receiving channel on said handle portion having right and left sidewalls and having a base formed by the surface of said handle portion; means for connecting said cartridge to said handle portion including:
    a series of outwardly extending projections disposed adjacent the outside surface of said right and left sidewalls of said fixed rack housing;

a plurality of openings in said handle portion base aligned to undercut said right and left channel walls, said openings receiving said fixed rack housing sidewall projections to lock said cartridge into position on said applier.

5. The cartridge of claim 1 further including:

right and left transfer fingers disposed at the front end of said fixed rack housing for transferring clips from the plane of the fixed rack housing base to the plane of a drive mechanism associated with said applier for delivering clips out of said cartridge into said applier;

separate support rods for each of said transfer fingers extending from the front end of said fixed rack housing and connecting to a side of its respective transfer finger to provide leaf spring bias action to hold said fingers in alignment with the base of said fixed rack housing and at the same time to provide torsion spring bias action to prevent said transfer finger from pitching about its own transverse axis;

tie bar means connecting the forward ends of said transfer fingers to restrict the independent movement of said transfer fingers.

6. The apparatus of claim 5 wherein said separate support rods extend axially from the front of said fixed rack housing base and then curve on a relatively large radius so as to extent transversely of said fixed rack housing base and to attach to said transfer fingers on their respective inside surfaces which face one another in opposed relationship.

7. The apparatus of claim 5 wherein each said transfer finger includes a generally wedge-shaped configuration with the apex of said wedge aligned generally with the base of said fixed rack housing and rising to a plane spaced vertically above the plane of said fixed rack housing base, said second plane extending axially for a short distance to the front end of each said transfer finger.

8. The apparatus of claim 7 wherein said transfer finger second plane includes a protrusion for engaging a portion of the clip and for holding the clip in position even though the applier drive mechanism may be moved slightly while the user is in the process of fixing a clip about a vessel to be ligated.

9. The apparatus of claim 5 wherein the leaf-spring portions of said separate support rods are joined together to form a single leaf spring portion.

10. The apparatus of claim 5 further including a U-shaped moving rack housing disposed in interlocking relationship with said fixed rack housing sidewalls and adapted for reciprocation axially along said fixed rack housing;

finger means disposed along the bases of both racks extending toward one another in confronting relationship for holding a plurality of clips in position therebetween.

11. The cartridge of claim 10 wherein said finger means projecting respectively from the bases of said fixed rack housing and said moving rack housing and formed integrally with said respective rack bases and positioned in apertures in the base and hinged from one edge of said aperture;

said hinge including a wedge-shaped brace to strengthen the hinge.

12. The cartridge of claim 10 wherein said finger means for said fixed rack housing and said moving rack housing includes separate strips having pairs of fingers stamped into them and having a plurality of flanges extending from their longitudinal sides and interlocking corresponding openings in the sides of said fixed rack housing walls and said moving rack housing walls to hold said metal strips in fixed alignment with the respective bases of said rack housings.

13. The apparatus of claim 10 wherein said axial guides include a forward end portion stepped vertically above the top of said axial guide to provide a stop against which the forward end of said moving rack housing will engage when it is in its forward-most position, said stepped up portion extending past the end of said transfer fingers;

a connecting bar connecting the forward ends of said stepped up portions of said guide rails.

14. The cartridge of claim 12 further including a detent tab extending from the outside surface of each of said stepped up portions of said guide rails adapted for engagement with a corresponding detent disposed on said multiple clip applier for holding the forward end portion of said fixed rack housing in proper vertical alignment with respect to said applier.

* * * * *